United States Patent
Greiner et al.

(10) Patent No.: US 9,250,104 B2
(45) Date of Patent: Feb. 2, 2016

(54) SENSOR FOR ACQUIRING PHYSIOLOGICAL SIGNALS OF A PATIENT

(75) Inventors: Harald Greiner, Aachen (DE); Bernd Wilm, Aachen (DE); Kai Hassing, Aachen (DE); Winfried Kaiser, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2364 days.

(21) Appl. No.: 11/569,823

(22) PCT Filed: Jun. 3, 2005

(86) PCT No.: PCT/IB2005/051812
§ 371 (c)(1),
(2), (4) Date: Nov. 30, 2006

(87) PCT Pub. No.: WO2005/122879
PCT Pub. Date: Dec. 29, 2005

(65) Prior Publication Data
US 2009/0118595 A1    May 7, 2009

(51) Int. Cl.
A61B 5/00 (2006.01)
G01D 21/00 (2006.01)
G06F 19/00 (2011.01)
A61B 5/021 (2006.01)
A61B 5/0402 (2006.01)
A61B 5/145 (2006.01)
H04W 8/26 (2009.01)
H04W 84/18 (2009.01)

(52) U.S. Cl.
CPC .............. *G01D 21/00* (2013.01); *A61B 5/0006* (2013.01); *G06F 19/323* (2013.01); *A61B 5/021* (2013.01); *A61B 5/0402* (2013.01); *A61B 5/145* (2013.01); *A61B 2560/0271* (2013.01); *A61B 2560/045* (2013.01); *H04W 8/26* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 5,335,664 A | 8/1994 | Nagashima | |
| 6,093,146 A | 7/2000 | Filangeri | |
| 6,175,752 B1* | 1/2001 | Say et al. | 600/345 |
| 6,287,252 B1* | 9/2001 | Lugo | A61B 5/1112 128/903 |
| 6,298,255 B1 | 10/2001 | Cordero et al. | |
| 6,643,531 B1 | 11/2003 | Katarow | |
| 2001/0039437 A1 | 11/2001 | Taepke et al. | |
| 2002/0013518 A1* | 1/2002 | West et al. | 600/300 |
| 2002/0045836 A1* | 4/2002 | Alkawwas | A61B 5/0006 600/509 |
| 2002/0109621 A1* | 8/2002 | Khair et al. | 341/174 |
| 2002/0115914 A1 | 8/2002 | Russ | |

(Continued)

FOREIGN PATENT DOCUMENTS

| DE | 103 01 225 A1 | 2/2004 |
|---|---|---|
| DE | 102 51 900 A1 | 5/2004 |

(Continued)

*Primary Examiner* — William Thomson
*Assistant Examiner* — Bobby Soriano (57) ABSTRACT

The present invention suggests the use of independent, wireless, smart and therefore self-contained sensors (3, 4, 5) in a patient monitoring system (1). The sensors (3, 4, 5) provide their own communication system for transmitting acquired signals to a patient monitor (8) etc. Furthermore a patient identifier (26) is associated to the communication. This approach introduces a patient-related concept, where all communication is personalized and assigned to the patient (2).

14 Claims, 2 Drawing Sheets

(56) References Cited

U.S. PATENT DOCUMENTS

| | | | |
|---|---|---|---|
| 2002/0120676 A1* | 8/2002 | Biondi et al. | 709/203 |
| 2002/0126036 A1* | 9/2002 | Flaherty et al. | 341/176 |
| 2002/0158775 A1* | 10/2002 | Wallace | 340/870.07 |
| 2003/0163287 A1 | 8/2003 | Vock et al. | |
| 2003/0167391 A1* | 9/2003 | Al-Ali | A61B 5/14551 713/153 |
| 2003/0187338 A1* | 10/2003 | Say et al. | 600/345 |
| 2003/0187618 A1 | 10/2003 | Inda et al. | |
| 2004/0199056 A1* | 10/2004 | Husemann et al. | 600/300 |
| 2005/0021376 A1* | 1/2005 | Zaleski et al. | 705/3 |
| 2005/0101841 A9* | 5/2005 | Kaylor et al. | 600/300 |
| 2005/0129240 A1* | 6/2005 | Balfanz et al. | 380/270 |
| 2005/0137464 A1* | 6/2005 | Bomba | 600/300 |
| 2005/0140964 A1* | 6/2005 | Eschenauer | H04L 63/1408 356/10 |
| 2005/0187789 A1* | 8/2005 | Hatlestad et al. | 705/2 |
| 2006/0126524 A1* | 6/2006 | Tateson | 370/252 |

FOREIGN PATENT DOCUMENTS

| | | |
|---|---|---|
| EP | 0 770 349 A1 | 5/1997 |
| GB | 2 348 726 A | 10/2000 |
| JP | 8010232 A | 1/1996 |
| WO | 02080762 A1 | 10/2002 |
| WO | 02093272 A1 | 11/2002 |
| WO | 03041425 A2 | 5/2003 |

* cited by examiner

SENSOR FOR ACQUIRING PHYSIOLOGICAL SIGNALS OF A PATIENT

The present invention relates to a sensor for acquiring physiological signals of a patient. Furthermore the invention relates to a patient monitoring system and to a method of operating such a sensor.

In a typical patient monitoring environment several sensors are attached to a patient's body. Thereby these different sensors, e.g. for acquiring ECG (electrocardiogram), $S_PO_2$ (oxygen saturation of arterial blood), temperature or NIBP (Non Invasive Blood Pressure) signals, are located at different locations on the patient. From these sensors physiological signals of the patient are transmitted via cable connections to a remote central station or monitoring system. If a wireless transmission technique is employed, e.g. using BAN (Body Area Network), a central transmitter also known as CCC (Central Communication Control) is worn by the patient. In this case all sensors are connected via cable to the central transmitter. Alternatively additional wireless communication links are employed between the sensors and the central transmitter, which needs to be independent of the communication link that is used to transmit all acquired signals from the patient to the monitoring system and/or the central station.

A disadvantage of known patient monitoring systems using wireless transmission techniques is the complex and time-consuming setup and control of each device within the monitoring system.

It is an object of the present invention to enable an easy to use patient monitoring technique.

This object is achieved according to the invention by a sensor for acquiring physiological signals of a patient, the sensor comprising a communication module adapted to provide independent wireless communication to a remote device, and a personalization module adapted to associate a patient identifier to said communication.

The object of the present invention is also achieved by a patient monitoring system, the system comprising at least one sensor for acquiring physiological signals of a patient, said sensor comprising a communication module adapted to provide independent wireless communication to a remote device, and a personalization module adapted to associate a patient identifier to said communication, the system further comprising at least one remote device connectable to said sensor using wireless communication.

The object of the present invention is furthermore achieved by a method of operating a sensor for acquiring physiological signals of a patient, wherein an independent wireless communication is established between the sensor and a remote device and a patient identifier is associated to said communication.

The object of the present invention is also achieved by a computer program comprising computer instructions to provide independent wireless communication from a sensor for acquiring physiological signals of a patient to a remote device, and computer instructions to associate a patient identifier to said communication, when the computer program is executed in a computer.

The present invention is based upon the concept of using independent, wireless, smart and therefore self-contained sensors. Thereby the invention is not restricted to a specific type of sensor. For example ECG, $S_PO_2$, NIBP, temperature or other sensors may be used with the present invention.

According to a first aspect of the invention the requirement for a specific patient worn device, such as a CCC, is eliminated. Signal acquisition at various locations on the patient and wireless communication are carried out independently using a self-contained sensor. Each sensor communicates independently with a remote device, i.e. a device, which is not connected to or worn by the patient, such as a patient monitor or a central station. There is a direct communication to the remote device without any intermediate patient-based station or the like. In other words, the sensor comprises its own communication system, e.g. a module for transmitting the acquired signals and/or derived data. This makes the application of the signal acquisition very flexible, especially as there are no interconnecting cables, which in addition improves as well the patient comfort. Different levels of surveillance can be easily achieved by applying additional or different independent sensors.

Any kind of wireless communication technique may be employed with the present invention, e.g. radiofrequency or optical communication. Examples for wireless communication techniques, which might be used, are Bluetooth, WLAN, infrared, ZigBee, UWB (Ultra Wide Bandwidth), NBFM (Narrow Band Frequency Modulation) etc. Network hubs may be employed to realize a "multi-hop" network and/or to switch to another communication technique (e.g. Ethernet, USB, RS232, WLAN, Powerline etc.)

According to a further aspect of the invention, a new general concept of patient monitoring using wireless communication is presented. Unlike the known monitoring techniques, where the former cable-based connections between monitoring equipment are merely emulated by wireless communication links, the new approach introduces a patient-related concept, where all communication is personalized and assigned to the patient. This is achieved by associating a patient identifier to the communication. In other words there is no communication without a direct and stringent connection to a specific patient. As a patient identifier a universal unique patient identifier (UUPID) is preferably used. With this new approach it can be assured, that signals acquired from a specific patient are transmitted, processed, stored, monitored etc. exclusively and definitely with reference to said patient. Furthermore this new technique of smart sensors allows a new patient monitoring concept, wherein monitoring equipment is not used in an old-fashioned cable- or room-oriented way. Instead the new concept allows easy to use patient monitoring in a very flexible way, allowing e.g. the movement of a patient from one room into another room without the need of handling or reconfiguring communication equipment.

The sensor according to the present invention preferably comprises a computer. The computer includes inter alia a central processor unit (CPU), a bus system, memory means, e.g. RAM or ROM, and input/output units. Preferably the computer comprises additional storage means. The technical effects necessary for operating a sensor according to the invention can thus be realized on the basis of the instructions of the computer program in accordance with the invention. Such a computer program can be stored on a carrier such as a CD-ROM or it can be available over the internet or another computer network. Prior to executing the computer program is loaded into the computer by reading the computer program for example by means of a communication link, and storing it in the memory of the computer.

These and other aspects of the invention will be further elaborated on the basis of the following embodiments which are defined in the dependent claims.

In a preferred embodiment of the invention the acquired signals and/or data derived from those signals are stored and/or processed within the smart sensor. In other words, the present invention preferably relates to a sensor for acquiring, storing and/or processing physiological signals of a patient. For this purpose the sensor comprises a signal storage and processing module. The signal storage and processing module preferably comprises storage means. This allows a sensor operation independent from the existence of a wireless link to a remote monitoring device. Furthermore the signal storage and processing module preferably comprises processing means, such as a microprocessor. In a further embodiment the smart sensor is adapted to control the processing and storing of signals and data depending on environmental conditions. For example the smart sensor may be adapted to store acquired signals and/or data derived therefrom for a prolonged time and to transmit those stored information when the communication link becomes available. Furthermore the type of signal processing may be adapted according to the availability of the communication link.

For providing electrical power to the signal storage and processing module as well as to all other parts of the smart sensor, the sensor preferably comprises a battery cell or the like.

In yet another preferred embodiment of the invention the sensor comprises a signal acquisition module adapted to autonomously control the signal acquisition. This preferably includes adapting the employed acquisition algorithm and/or acquisition strategy. In other words the signal acquisition of the sensor is controlled by the sensor itself without any interaction with an external device etc. Employing smart controls and settings of control parameter to the sensor improves their independence even further, especially for scenarios in which their communication link does not exist continuously. Preferably, the signal acquisition module is additionally controllable by a remote device using an existing communication link. In this case the signal acquisition in case of an incorrect or lost communication link may be controlled by commands and instructions send to the sensor prior to the communication link failure.

According to another embodiment of the invention the communication module of the sensor is adapted to autonomously control the wireless communication with the remote device. Preferably the control is carried out depending on internal and/or external conditions. For example a specific control algorithm is implemented that allows trading bandwidth vs. range vs. power consumption.

According to still another embodiment of the invention the personalization module of the sensor is adapted to create the patient identifier. This is preferably the case, if no equipment is currently assigned to a patient. Then, the first smart sensor creates a new patient identifier, which preferably is subsequently copied into other equipment (e.g. smart sensors or remote devices) that is newly assigned to the same patient. In a preferred embodiment a universal unique identifier UUID (a 64 bit universal unique identifier coordinated through the IEEE) assigned e.g. by the manufacturer to each device used within the monitoring system is employed to create the new patient identifier.

A smart sensor according to the present invention is easy to use and offer a high flexibility. Because of its smartness the sensor can adapt itself to its use and environment with little or no user intervention.

These and other aspects of the invention will be described in detail hereinafter, by way of example, with reference to the following embodiments and the accompanying drawings; in which.

Figure 1:
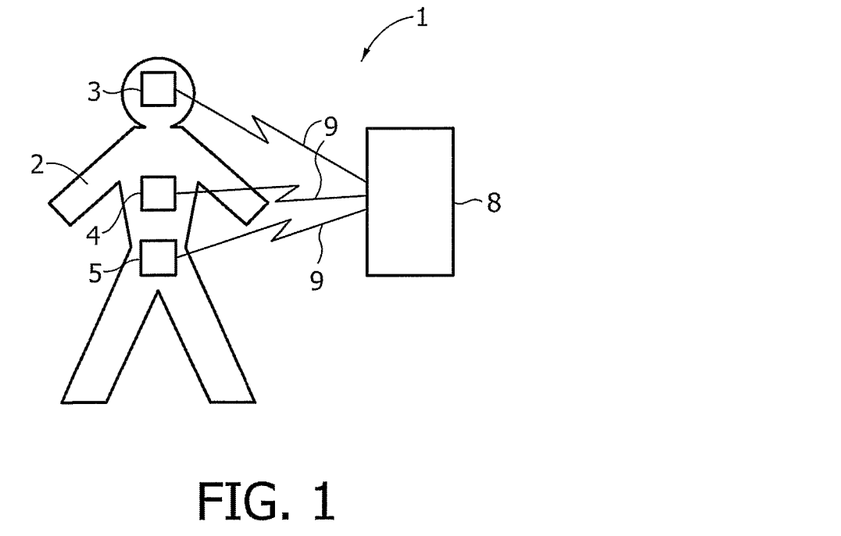
FIG. 1 is a block diagram showing an overview of a patient monitoring system.

FIG. 1 illustrates a system 1 for monitoring a patient 2 in a hospital's room. An ECG sensor 3, a $S_pO_2$ sensor 4 and a NIBP sensor 5 are attached to the patient's body. Each sensor 3, 4, 5 comprises hardware and software components which allow the sensor to operate autonomously and independent from other devices, see FIG. 2. Multiple of these smart sensors can be placed independently at various locations on the patient's body, e.g. head, chest, pelvis, wrist, arm or leg etc.

From each smart sensor 3, 4, 5 all the measurement data of the patient 2 are transmitted directly to a remote device. For this purpose each smart sensor 3, 4, 5 comprises a communication module 6 comprising a RF transceiver 7. No patient-worn transmitter or the like is employed. In the present embodiment the remote device is a central response center or a patient monitor 8 dedicated to that patient. In operating mode the patient monitor 8 is connected via wireless communication links 9 to the smart sensors 3, 4, 5. The patient monitor 8 is adapted for processing and displaying the acquired signals. In the present embodiment the step of processing the acquired signals is carried out within the sensors 3, 4, 5. The patient monitor 8 merely displays the processed data received from the sensors 3, 4, 5 on its monitor.

Figure 2:
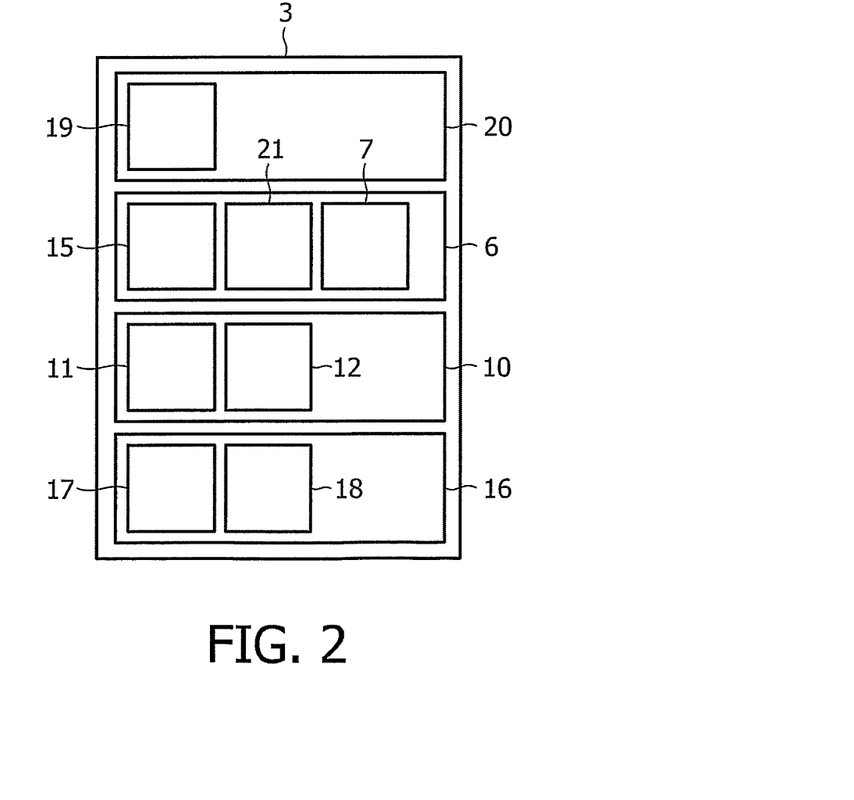
FIG. 2 is a block diagram of a smart sensor.

In the present embodiment all smart sensors 3, 4, 5 know for which patient 2 they are acquiring signals. For this purpose a universal unique patient identifier (UUPID) is assigned to the communication by a personalization module 10 of the smart sensor 3, 4, 5. The assignment of the UUPID to the communication is realized in a way such each information (e.g. each data packet) transmitted between communication partners can be associated to a UUPID. If connection-oriented protocols are used, the UUPID is assigned to the logic connection. All data related to this connection are associated to this UUPID. This applies to datagram-oriented protocols as well, if and to the extend to which data packet can assigned to a logic connection.

The personalization module 10 comprises a UUPID storage 11, where the UUPID is stored. If a smart sensor is assigned to a patient 2 that already has other equipment (e.g. patient monitor or other smart sensors) assigned, the UUPID of that patient 2 is stored in the UUPID storage 11 of said newly activated smart sensor. If no equipment is currently assigned to a patient, the first smart sensor creates a new UUPID by means of a UUPID creator 12, which is preferably implemented as part of the personalization module 10. This UUPID is subsequently copied into other equipment (e.g. smart sensors) that is newly assigned to the same patient. For creating a new UUPID a universal unique identifier UUID is used, preferably by appending a unique value that is incremented each time a UUPID is generated. For assigning the UUPID to the communication the personalization module 10 is connected to the communication module 6 of the smart sensor.

Figure 4:
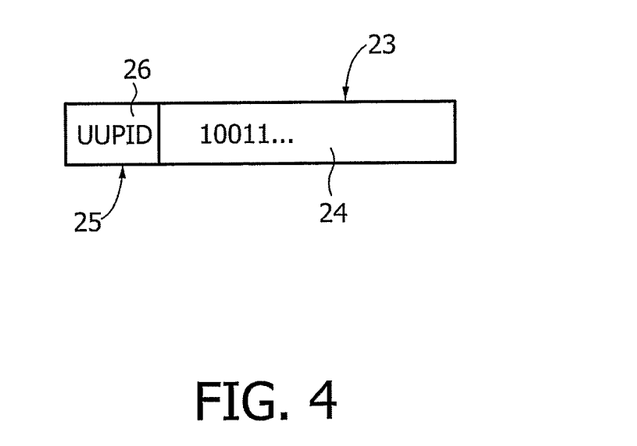
FIG. 4 is a schematic illustration of a transmitted data block.

Preferably the UUPID is transmitted just one time for each established communication link between the smart sensor 3, 4, 5 and a remote device, e.g. the patient monitor 8. If the UUPID is communicated to all communication partners all data subsequently transmitted is linked to this UUPID. In the present embodiment the transmission of the UUPID is realized in a way that the first data block 23 transmitted between the smart sensor 3, 4, 5 and the patient monitor 8 comprises acquired signal data 24 and a header 25 containing UUPID information 26, see FIG. 4. Said UUPID information 26 is transmitted internally from the personalization module 10 to the communication module 6 prior to communication. Alternatively the UUPID is transmitted with each data packet.

Preferably additional data, such as patient demographics, is linked to the UUPID, i.e. stored with it in the UUPID storage 11. Examples of such patient demographics are: unique identifier used in that application, e.g. a Medical Record Number (MRN) and/or Social Security Number (SSN) or other attributes to help identify the patient such as name and gender. These patient demographics are preferably used to resolve situations where users inadvertently assigned smart sensors 3, 4, 5 and/or other equipment to a patient 2.

Preferably the smart sensor 3, 4, 5 is used to transfer data linked to the UUPID to a patient monitor 8 for use by that monitor. Furthermore the smart sensor 3, 4, 5 is adapted to receive linked data transferred from the patient monitor 2 for use by the smart sensor. Preferably linked data is automatically transferred from one patient monitor 8 to another patient monitor 8' that subsequently is used for the same patient 2 by using the smart sensor(s) 3, 4, 5 for transporting that linked data, see FIG. 3.

Using UUPIDs in the smart sensors instead of other (e.g. equipment related) identifiers allows for better support of flexible application scenarios. If for example a patient 2 is already assigned to a patient monitor 8, i.e. that patient monitor 8 already created a UUPID and keeps additional patient demographics linked to it. That patient monitor 8 detects a newly activated sensor 3' and the sensor 3' detects only that patient monitor 8, see FIG. 3. Then it is extremely likely that this smart sensor 3' should be assigned to that same patient 2. Preferably that assignment is proposed to the user (e.g. at that patient monitor). Depending on the application a confirmation step can be omitted, if that assignment is evident to the user and can be reverted in the unlikely case it was not intentional.

Figure 3:
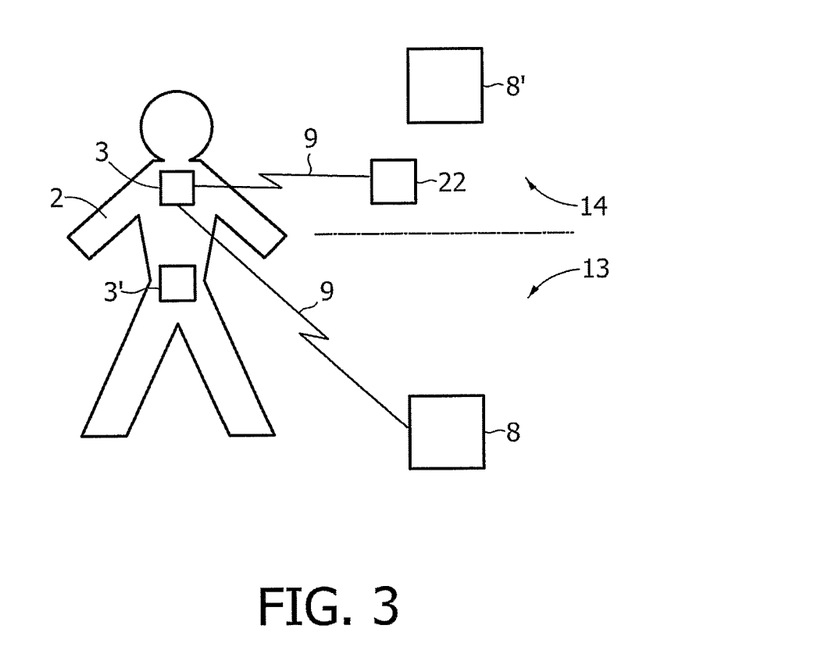
FIG. 3 is a block diagram of an application scenario.

In another case a patient 2 with an assigned smart sensor 3 is moved from a first room 13 to a different location, e.g. another room 14 of the hospital. At that location a patient monitor 8' is used that has currently no patient assigned. If this is the only patient monitor detected by the smart sensor (and the previous monitor 8 is no longer reachable) then it is very likely that the smart sensor 3 should be assigned to that new patient monitor 8'. This again is done with or without confirmation depending on the application.

In case a newly activated smart sensor detects more than one patient monitor, it then preferably triggers a confirmation dialog at each of those patient monitors simultaneously. The smart sensor is preferably assigned to the patient monitor that gets the confirmation first. Preferably, the smart sensor subsequently triggers all other patient monitors to remove the confirmation dialog. Should no confirmation be received after a timeout the smart sensor may deactivate itself (if such a function is available) and/or stay unassigned or a user may re-activate that sensor triggering its assignment. Alternatively, equipment providing a user interface (e.g. a patient monitor) displays (upon user request) a list of all unassigned smart sensors that it detects.

The smart sensor's communication module 6 preferably provide displaying means 15, e.g. optical display (LED etc.), to show its status (un-assigned, assigned) to help to increase the user confidence by reassurance of that status. Preferably data linked to the UUPID (e.g. patient name) is displayed in a LCD display or the like.

In a further embodiment the communication module 6 of the sensors 3, 4, 5 is adapted to provide an optical signal, e.g. are adapted to control a build-in diode (LED) or the like to flash, if a user initiates a sensor request. In case a user wishes to know which sensors are assigned to a specific patient monitor 8 or to a patient 2, he may initiate this request e.g. by pressing a button on the touch screen of the patient monitor 8. The patient monitor 8 is adapted to send the request via the communication link 9 to the sensors 3, 4, 5.

Each sensor 3, 4, 5 comprises a signal storage and processing module 16 comprising a data storage 17, such as removable memory cards, smart cards or hard-wired memory devices, and a microprocessor 18 executing computer program code. The smart sensor 3, 4, 5 provides the capability to store acquired signals and status information during its operation. This preferably includes real-time data as well as trended data (averaged or specific samples collected at lower sample frequencies). Thus the smart sensor 3, 4, 5 operates fully independently of the existence of a wireless communication link 9. Even a relative limited storage capability can be used very effectively.

If the ECG sensor 3 measures continuously wave(s) and derived real-time value(s) from it, it preferably stores all that data into a data storage 17 in form of a ring buffer. If the communication link 9 is disrupted for a short time all the data in the ring buffer is transmitted as soon as the communication link 9 is restored.

However, there are many application scenarios where the wave(s) are usually of no interest to the user. Therefore that data is preferably not transmitted (saving communication bandwidth) and usually also not stored in the ring buffer. This extends the time for data that can be recovered greatly as the amount of storage to keep a wave compared to a measurement value that is derived from it may vary by a factor of 100.

If recovery of data of even longer time periods is useful in certain applications then deriving trend values from the real-time measurement values in the smart sensors 3, 4, 5 is advantageous, because the storage requirements for trend values are again far smaller than for the derived values themselves (e.g. factor of 10 to 100 depending on the trend resolution provided).

Data stored in the ring buffer is preferably used also to provide that data later to equipment (e.g. a patient monitor 8) to which the smart sensor 3, 4, 5 is connected subsequently. E.g. data acquired, processed and trended during surgery in the operating room or during a procedure is transmitted to a patient monitor in the intensive care unit used to monitor subsequently the same patient 2.

Any real-time or trend measurement data stored on the smart sensor 3, 4, 5 (and/or any other equipment 8) is preferably safely linked to a patient via the UUPID. This greatly helps to safely merge data of one specific patient at a point in the monitoring system for a continuous and complete patient record.

The smart sensor 3, 4, 5 comprises smart controls and settings, which are especially helpful for scenarios in which the communication link 9 does not exist continuously. This could be the case in situations in which inherently (due to the scenario) communication is not available for a prolonged time (e.g. patient 2 is transported from the operating room to the intensive care unit without using a transport monitor) or situations with short (and maybe unexpected) communication interrupts, e.g. due to RF disturbance, a battery that needs to be replaced or recharged or unexpected outage of the equipment receiving the data (e.g. a patient monitor automatically restarting due to an unexpected software error or a short outage of main power until backup power system of the hospital is activated). For this purpose a controller 19 is provided in the smart sensor's acquisition module 20. The controller 19 is adapted to autonomously control the signal acquisition. This includes adapting the employed acquisition algorithm and/or acquisition strategy. For this purpose the controller 19 preferably comprises a microprocessor executing computer program code.

Smart sensors 3, 4, 5 in such situations preferably continue to fully operate and even autonomously adapt their measurement algorithm according to predefined criteria. These criteria are preferably reflected by the controls such smart sensors offer and retained in their settings. Examples for such criteria are: a timing sequence of aperiodic measurements (e.g. take a NBP measurement every 15 minutes), intervals of continuous measurements with sleep periods to save power (e.g. $S_PO_2$ measurement every 5 minutes for 30 seconds) or basically any other method known from systems that rely on the existence of a communication link 9 between the sensor 3, 4, 5 and a device executing the measurement algorithm.

Smart sensors loosing their communication link 9 can according to the invention either simply continue their signals acquisition using the same criteria or switch to another method that is more appropriate for that situation. The switching is preferably performed after a certain period of time after the loss of the communication link. Alternatively, the switching is influenced by other factors such as available resources (e.g. buffer size, estimated time to operate on the available power source). Preferably intelligent algorithms, based on measured values, are used to e.g. capture critical episodes but still optimizing the power consumption and/or memory required for data kept in the ring buffer for subsequent transmittal if a communication link 9 is available.

The communication module 6 comprises a controller 21 adapted to implement application specific algorithms to control the wireless communication link 9. Preferably the controller 21 comprises a microprocessor executing computer program code and allows trading bandwidth vs. range vs. power consumption. Such a smart sensor adapts itself automatically to a broad variety of different application scenarios.

In case smart sensors 3, 4, 5 are assigned to a patient 2 who is prepared in the induction room 13 for a surgery. These smart sensors are assigned to a (usually lower end) patient monitor 8, see FIG. 3. The patient is moved into the operating room 14 that usually is located close to the induction room 13. However, the RF signal is attenuated due to loss of line of sight (e.g. due to walls). When the patient 2 reaches the operating room 14 communication to a (usually higher end) patient monitor 8' will be established. The smart sensor 3 trades the bandwidth during such a transitional period for extended communication range (to overcome physical range and the potential signal attenuation by e.g. walls) and transmits only a selected subset of data.

In the present case the smart sensor 3 is adapted to transmit only the measurement values and no wave data, which reduces the required bandwidth substantially. As soon as the smart sensor 3 can establish a communication link 9 with sufficient bandwidth all data can be transmitted again. This can be done seamlessly without user intervention.

Preferably the communication range and/or the required bandwidth is automatically reduced if communication suffers. This helps using the shared RF environment at its optimum.

Assume an intensive care unit with multiple patients 2 in close proximity, all of them assigned to a higher end patient monitor 8 that receives data from smart sensors 3, 4, 5 assigned to those patients 2. As the smart sensors 3, 4, 5 detect that situation (detect multiple patient monitors and sensors not assigned to the same patient as themselves) they preferably cut back their required bandwidth and/or their communication range.

If the flexibility of the communication module 6 is high enough the same smart sensor 3, 4, 5 can be used to communicate with a patient monitor 8 that is usually close to the patient and alternatively directly with a central station (not shown) usually located further away.

Other equipment of the monitoring system 1 is preferably adapted to passive listen to communication from smart sensors 3, 4, 5 to equipment (e.g. patient monitor 8) that is assigned to the same patient.

Smart sensors 3, 4, 5 preferably communicate to one patient monitor 8 at a time (see the scenario depicted in FIG. 3). However, the patient monitor 8' currently not communicating with the smart sensor 3 is preferably adapted to passively listen to that communication and (already or still) receiving the measurement data of the smart sensor 3. That passively received data can of course be displayed, stored, forwarded otherwise processed, e.g. to annunciate alarms. This greatly enhances the flexibility and usability of the systems for the medical staff.

In case that caregivers need to make rounds in an intensive care unit, walking from patient to patient, they preferably carry a handheld device 22 (similar to a small patient monitor) that is used e.g. as a viewer for the measurement information communicated by smart sensors 3, 4, 5. That device 22 preferably comprises a microprocessor executing computer program code and provides a mode of operation that is optimized for that purpose. It preferably tunes automatically to all smart sensors 3, 4, 5 of a patient 2, if only one at a time can be detected. If sensors or equipment assigned to different patient are detected simultaneously, it preferably offers a selection list of those patients to the user. This is preferably done using the data linked to the UUPID (e.g. patient name). I.e. as the caregiver walks from patient to patient the device 22 either automatically tunes to that patient (if they are e.g. located in different rooms) or the user can trigger a patient selection menu when moving to the next patient. That patient menu is usually rather short compared to the number of all patients in that whole clinical unit. This again improves the ease of use and reduces the likelihood of operator errors.

In this scenario the use of such a device 22 is preferably independent of the fact that smart sensors 3, 4, 5 whose measurement information is received are communicating already to another equipment (e.g. patient monitor 8) for primary use or not.

The purpose of such a device 22 also needs not to be restricted to a viewing function. E.g. it is preferably useful to use such a device on a round to gather measurement information (real-time or trended) which is later transferred into e.g. a system at a central location.

All scenarios in which the patient 2 is transported to other locations in the hospital benefit as well from the fact that handheld devices 22 can receive measurement information from the patient's smart sensors 3, 4, 5 irrespectively if those smart sensors 3, 4, 5 are communicating already to another equipment (e.g. patient monitor 8) for primary use or not. I.e. a viewing device 22 can be used during transport without interfering with other equipment assigned to the same patient 2. This is especially beneficial at the locations where the patient transports starts (e.g. emergency room) and ends (e.g. intensive care unit) allowing an automatic and smooth handover of the patient. I.e. the device 22 used for transport as well as the stationary patient monitor 8 can receive the measurement information for the interim period during handover. This improves again the ease of use, as medical staff is not required to act in any way with either equipment. This allows the medical staff to dedicate their full attention to transferring responsibility for the patient and any information about the patient status to the receiving team. Nonetheless no measurement information from the patient's smart sensors 3, 4, 5 will be lost or could inadvertently be mixed up with other measurement information not belonging to that same patient.

Preferably such handheld device 22 is adapted to setup the smart sensors 3, 4, 5 where no patient monitor 8 with smart sensor support is available (e.g. in an emergency room).

A smart sensor 3, 4, 5 according to the present invention may be activated by turning on power. This can be achieved by, e.g. closing or opening a switch or pushing a button, adding a battery or other power source. Another way of activating the smart sensor is the detection of placement to patient's body by mechanical, electrical, optical or other physical means. Here a direct physical contact to skin or body may be detected, e.g. if a mechanical switch is closed or opened or button is pushed, when sensor is applied to a surface or in case of a capacitive detection of the body or by measuring the reflection of light from the body or by detection of the body temperature. Alternatively the attachment of the sensor to the patient is detected indirectly, e.g. by closing a clip stuck onto a finger or by closing a band used to attach the sensor (e.g. on the wrist).

Other methods to activate the smart sensor 3, 4, 5 are prior intentional movement of the sensor with a specific characteristic (e.g. shaking) before application to the patient or detection of the removal of a part prior to the attachment of the sensor to the patient (e.g. removal of strip to expose adhesive tape used for fixation to the patient or removal of strip or other part to activate the battery of the smart sensor).

Still other methods to activate the smart sensor 3, 4, 5 are detection of a valid signal source, e.g. ECG-lead detection, wakeup signal received through wireless communication, e.g. sent by a patient monitor to find and activate all smart sensors in its vicinity or automatic detection of the presence of other equipment or smart sensors that are already assigned to a patient.

Receiving a RF signal, that is not related to known active communication, usually is used to triggers the detection of the presence of other wireless communication devices. Passive listing to all communication already may unveil the identity of other devices belonging to the system. An alternative or additional method of detection is to try to establish communication to those yet unknown devices to positively identify them as belonging to the system.

It is understood that sensors 3, 4, 5 may refer to re-usable as well as single use (for one patient) sensors. "Transmit" and "receive" are used in a logical sense, indicating the flow of measurement data. I.e. it is obvious that bidirectional communication is needed to transmit and receive data, control and status information. This may apply both for application related information (i.e. sensor/measurement related information) and for purely communication related information (e.g. acknowledgement of received data or repetition of lost data).

In a preferred embodiment of the present invention a joint time base (date and time) is established and used by all sensors, patient monitors and central stations of the patient monitoring system. The time base is preferably based upon the Network Time Protocol (NTP) Version 3 known from the RFC 1305 standard. Alternatively other techniques may be used as well.

Preferably the sensor according to the present invention comprises at least one microprocessor adapted to execute computer program code (operating software) in order to carry out the present invention. The present invention may be implemented in a way that each module 6, 10, 16, 20 of the sensor 3, 4, 5 comprises a microprocessor. Alternatively the sensor 3, 4, 5 comprises a single microprocessor system to coordinate and perform all operational steps as described above.

Preferably the operating software of the sensors 3, 4, 5 may be upgraded or updated using solely the sensor's wireless communication link 9. If the sensors 3, 4, 5 provide additional storage to hold a second version of their operating software that new software version (upgrade or update) is preferably transferred from a remote device to each sensor in the system 1 using any available (i.e. otherwise unused) wireless bandwidth. Whenever all sensors 3, 4, 5 correctly received and stored that new version they can then be instructed to execute that new version. A subsequent upgrade or update can then overwrite the first storage and instruct the sensor to continue to use again that first storage.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" does not exclude a plurality, and that a single element, such as a computer system or another unit may fulfil the functions of several means recited in the claims. Any reference signs in the claims shall not be construed as limiting the claim concerned.

| REFERENCE LIST | |
|---|---|
| 1 | monitoring system |
| 2 | patient |
| 3 | sensor |
| 4 | sensor |
| 5 | sensor |
| 6 | communication module |
| 7 | RF transceiver |
| 8 | patient monitor |
| 9 | wireless communication link |
| 10 | personalization module |
| 11 | UUPID storage |
| 12 | UUPID creator |
| 13 | first room |
| 14 | second room |
| 15 | display |
| 16 | signal storage and processing module |
| 17 | data storage |
| 18 | processor |
| 19 | controller |
| 20 | acquisition module |
| 21 | controller |
| 22 | handheld device |
| 23 | data block |
| 24 | signal data |
| 25 | header |
| 26 | UUPID |

The invention claimed is:

1. A patient monitoring system comprising:
a plurality of self-contained sensors which acquire physiological signals from a patient and a remote device which wirelessly communicate with the sensors, wherein each of the plurality of sensors includes:
a communication module which provides direct and independent wireless communication to the remote device without any intermediate patient-based station,
a personalization module configured to create and associate a patient identifier to said communication, and a signal storage and processing module which stores and process the acquired signals and data derived from the signals respectively prior to communication with the remote device, wherein the signal storage and processing module further controls processing and storing of signals and data depending on the availability of the communication, wherein each sensor communicates independently with the remote device.

2. The system as claimed in claim 1, wherein the communication module autonomously controls the communication with the remote device.

3. A patient monitoring system, comprising:

a plurality of self-contained sensors configured to acquire physiological signals from a patient and a remote device configured to wirelessly communicate with the sensors, wherein each of the plurality of sensors includes:

a communication device configured to provide direct and independent wireless communication to the remote device without any intermediate patient-based station, a computer in the sensor configured to:

create and associate a patient identifier to said communication, store and process the acquired signals and data derived from the signals respectively prior to communication with the remote device, control processing and storing of signals and data depending on the availability of the communication, wherein each sensor is configured to communicate independently with the remote device, wherein the communication is a direct communication to the remote device.

4. A method of operating a plurality of sensors for acquiring physiological signals of a patient comprising:

attaching each sensor to a patient, the sensors each acquiring corresponding physiological data from the patient;

creating a patient identifier within at least one of the sensors;

assigning the patient identifier to each sensor;

in each sensor, processing the acquired physiological data with each sensor;

in each sensor, forming the acquired physiological data into a corresponding physiological data communication from each sensor;

in each sensor, inserting the patient identifier into a header of each physiological data communication;

storing each physiological data communication in the corresponding sensor until a remote patient monitoring device is available;

finding an available remote patient monitoring device;

with each sensor, initiating a wireless communication link directly and independently from each sensor with the available remote patient monitoring device; and wirelessly communicating the physiological data communication with the patient identifier from each sensor to the available remote patient monitoring device.

5. A method of monitoring a patient comprising:

attaching a plurality of autonomous sensors to a patient, each sensor acquiring physiological data from the patient;

creating a patient identifier within one of the plurality of sensors;

with wireless communication among the plurality of sensors, assigning the patient identifier to other sensors attached to the patient;

with one of the plurality of sensors, detecting one or more unassigned remote monitoring devices that are not assigned to a patient;

with one of the plurality of sensors, establishing a wireless communication link to one of the unassigned remote monitoring devices; and with one of the plurality of sensors, wirelessly receiving a confirmation signed from the unassigned remote monitoring device;

with one of the plurality of sensors, assigning the sensors with the created patient identifier to the unassigned remote monitoring device;

wirelessly communicating physiological data and the patient identifier from the plurality of sensors to the remote monitoring device.

6. The method of claim 5 further including:

assigning one or more additional sensors to the patient and automatically copying the assigned patient identifier to the one or more additional sensors.

7. The method of claim 5 further including:

storing the physiological data acquired by each sensor in a signal storage and processing module of the sensor;

monitoring communication environmental conditions;

based on the monitored communication environmental conditions, changing at least one of a physiological data acquisition algorithm and properties of the communication link with the signal storage and processing module of the sensor.

8. A handheld device for monitoring each of a plurality of patients comprising:

a receiver which wirelessly receives communications which each include patient data and patient identifiers directly from a plurality of sensors associated with a plurality of patients;

a display which displays the patient data for a selected patient;

a processor which:

receives the communications from the receiver corresponding to the plurality of sensors, determines the patient identifier from each communication, and controls the display to display only the patient data from a selected one of the plurality of patients based on the patient identifier corresponding to the selected one of the plurality of patients until triggered to display patient data from a different one of the plurality of patients, wherein the receiver passively listens for the communications from the plurality of sensors and automatically tunes to all of the sensors assigned to the patient identifier corresponding to the selected patient; and each sensor is configured to create a patient identifier and associate the patient identifier with its communications.

9. The handheld device of claim 8, wherein the processor automatically updates the display, the patient identification, and associated patient data when a communication with a different patient identifier is received.

10. The handheld device of claim 8, wherein the trigger is automatic based on the data received.

11. The handheld device of claim 8, wherein the trigger is manually activated.

12. The method of claim 5, further including:

after receiving a first confirmation signal from the one of the unassigned remote monitoring devices, notifying any unassigned remote monitoring devices from which another confirmation signal is subsequently received.

13. The method according to claim 5, further including:
in response to detecting more than one remote monitoring device, triggering a confirmation dialog with each of the detected remote monitoring devices.

14. A non-transitory computer readable medium which carries software to control one or more processors disposed in patient sensors for performing the method comprising:
with the patient worn sensors, acquiring physiological data from a patient;
creating a patient identifier with the one or more processors of one of the patient worn sensors;
using wireless communication among the patient sensors worn by the patient, assigning the patient identifier to the other patient sensors worn by the patient;
with the patient sensors worn by the patient, detecting a remote monitoring device which is not assigned;
with the patient sensors, autonomously assigning the patient sensors to the detected remote monitoring device;
wirelessly communicating physiological data and the patient identifier from the patient worn sensors to the assigned remote monitoring device.

* * * * *